(12) United States Patent
Iliopoulos et al.

(10) Patent No.: US 6,288,137 B1
(45) Date of Patent: *Sep. 11, 2001

(54) PROCESS FOR PREPARING AN AQUEOUS COMPOSITION IN GEL FORM AND COMPOSITIONS OBTAINABLE FROM THIS PROCESS, ESPECIALLY A COMPOSITION CONTAINING VESICLES, IN PARTICULAR LIPOSOMES

(75) Inventors: Ilias Iliopoulos, Paris; Anne Cartalas-Sarrazin, Issy-les-Moulineaux; Karine Loyen, Le Havre; Roland Audebert, St Leu la Foret; Alain Meybeck, Courbevoie; Jean-François Tranchant, Marigny-les-Usages, all of (FR)

(73) Assignee: LVMH Recherche (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/854,413

(22) Filed: May 12, 1997

Related U.S. Application Data (63) Continuation of application No. 08/592,319, filed as application No. PCT/FR94/00971 on Aug. 2, 1994, now abandoned.

(30) Foreign Application Priority Data

Aug. 4, 1993 (FR) .................................................. 93/09607

(51) Int. Cl.[7] .............................. C08K 5/06; C08L 33/02; C08L 33/24; A61K 7/00
(52) U.S. Cl. ........................... 523/105; 524/376; 524/394; 524/236; 524/555; 524/556; 424/70.31; 424/450
(58) Field of Search .................................... 524/376, 378, 524/261, 555, 556, 394; 523/105; 424/450, 70.31

(56) References Cited

U.S. PATENT DOCUMENTS

| | | | |
|---|---|---|---|
| 5,156,766 | * 10/1992 | Behan et al. | 424/450 |
| 5,171,772 | * 12/1992 | Hoy et al. | 524/457 |
| 5,204,105 | * 4/1993 | Mausner | 424/450 |
| 5,268,180 | * 12/1993 | Morancais et al. | 424/450 |
| 5,429,820 | * 7/1995 | Kamitani et al. | 424/70.31 |
| 5,719,206 | * 2/1998 | Mihoya et al. | 524/261 |

FOREIGN PATENT DOCUMENTS

| | | |
|---|---|---|
| 0057875 | 8/1982 | (EP) . |
| 0346995 | 12/1989 | (EP) . |
| 2166107 | 4/1986 | (GB) . |
| 8700848 | 2/1987 | (WO) . |
| 9108280 | 6/1991 | (WO) . |
| 9220735 | 11/1992 | (WO) . |

OTHER PUBLICATIONS

Progress in Colloid & Polymer Science, vol. 89, 1992, Darmstadt, DE pp. 118–121, Magny B. et al.—"Interactions between Hydrophobically Modified Polymers and Surfactants".

Journal of the Chemcal Society, Faraday Transactions, vol. 86, No. 12, 1990, London pp. 2253–2261, Strey R. et al.—"Dilute Lamellar and L3 Phases in the Binary Water—C12E5 System".

* cited by examiner

Primary Examiner—Tae Yoon
(74) Attorney, Agent, or Firm—Bierman, Muserlian and Lucas

(57) ABSTRACT

The present invention concerns a process for preparing an aqueous composition in the form of a gel at a given temperature.

The process is characterized in that an associative water-soluble polymer constituted by a hydrophilic main chain and hydrophobic pendant groups is brought into the presence, in said composition, of at least one surfactant in the form of bilayers when it is in aqueous solution under the same temperature and concentration conditions.

Compositions in the form of gels or liquids are thus obtained.

37 Claims, 9 Drawing Sheets

PROCESS FOR PREPARING AN AQUEOUS COMPOSITION IN GEL FORM AND COMPOSITIONS OBTAINABLE FROM THIS PROCESS, ESPECIALLY A COMPOSITION CONTAINING VESICLES, IN PARTICULAR LIPOSOMES

This is a continuation divisional of Application Ser. No. 08/592,319 filed Mar. 4, 1996 now abandoned, which is a 371 of PCT/FR94/00971 filed Aug. 2, 1999.

The present invention concerns a novel process for preparing an aqueous composition in the form of a gel and to novel compositions which can be obtained from this process, especially compositions containing vesicles, in particular liposomes.

Water-soluble polymers have numerous applications in a wide variety of industrial fields such as cosmetics, enhanced oil recovery, and food additives.

They are often used to control the rheology of aqueous formulations, since only a little dry material is needed to produce highly viscous solutions or even gels. A particular class of those water-soluble polymers is associative water-soluble polymers.

Two recent works are cited here which particularly concern that type of polymer: "Water Soluble Polymers", ACS Symposium Series 467, ed. Shalaby W Shalaby et al., Am. Chem. Soc. Washington (1991), pp. 82–200, and "Polymers in Aqueous Media", ed. J. Edward Glass, Advances in Chemistry Series no. 223, Am. Chem. Soc. Washington D.C. (1989).

Associative polymers are polymers constituted by a hydrophilic main chain and hydrophobic side chains which are relatively few in number compared with the hydrophilic units of the main chain. Their behavior in solution is a result of competition between the hydrophobic and hydrophilic properties of their structure. The hydrophobic units tend to form aggregates constituting linkage points between the macromolecular chains.

From a Theological viewpoint, associative water-soluble polymers have a very high viscosifying power in water, retain their viscosity well in a saline medium, and exhibit reversible behavior under stress (rheofluidifying).

The study of aqueous systems containing polymers and surfactants is very important because of the numerous industrial applications in a wide variety of fields such as paint, cosmetics, or enhanced oil recovery.

In those systems, mixed polymer/surfactant aggregates can form, which are stabilized by different types of interactions: electrostatic interactions, dipolar interactions, or hydrogen bonds. Associative water-soluble polymers can interact more specifically with surfactants due to their hydrophobic portions.

The following publications: I. Iliopoulos et al., Langmuir 1991, 7, 617; and B. Magny et al., Prog. Colloid. Polym. Sci., 1992, 89, 118, show that the addition of a cationic, anionic, or non ionic surfactant to a hydrophobically modified sodium polyacrylate solution causes an increase in viscosity.

U.S. Pat. No. 4,432,881 describes an aqueous liquid medium with increased viscosity obtained by dispersing a water-soluble polymer containing hydrophobic pendant groups and a surfactant in that medium. The medium can in particular be used for enhanced oil recovery.

S. Evani and G. D. Rose, Proc. Am. Chem. Soc. Div. of Polym. Mater. Sci. and Eng., 1987, 57, 477 describes two systems which use reversible hydrophobic combinations to control the rheology respectively of paints containing latex and of aqueous fluids for enhanced oil recovery.

For the surfactant associative polymer couples concerned, those two documents show the favorable effect on the viscosity of the medium either of an increase in temperature or of an increase in the salt concentration in the medium.

Further, a number of studies have been devoted to the determination of interactions and phase transitions in water-surfactant systems as a function of temperature and surfactant concentration.

Particular interest has been taken in systems in which the surfactant is a polyethyleneglycol monoalkylether with formula:

$$H(CH_2)_i(OCH_2CH_2)_jOH$$

hereinafter termed $C_iE_j$ where i represents the number of carbon atoms in the alkyl chain and j represents the number of ethylene oxide groups contained in the polar head of the surfactant.

Those surfactants have the particular property of having a low segregation temperature: there is a temperature above which the micellar solution separates into two phases, one of which is dilute and the other of which is concentrated in surfactant. This temperature is termed the cloud temperature. This phenomenon is due to a reduction in hydration of the ethylene oxide groups when the temperature increases. As a result, the longer the ethyleneglycol chain, the higher the segregation temperature.

At relatively high temperatures and very low concentrations, liquid crystal phases are observed (which constitute a further specific property of those surfactants): a lamellar phase $L_\alpha$, which persists up to very high dilutions (concentrations of the order of 1% by weight for $C_{12}E_5$), two phases $L_3$ and $L_\alpha^+$ constitute bilayers, and finally several regions of liquid-liquid coexistence have been shown to exist.

Phase diagrams of the surfactants $C_{12}E_3$, $C_{12}E_4$ and $C_{12}E_5$ have been published in the literature (see D. G. Hall, J. T. Tiddy, "Anionic Surfactants: Physical Chemistry of Surfactant's Action; Schick, M. J., Ed., Marcel Dekker, New York 1987, pp 55–108). More recently, a study concerning the surfactant $C_{12}E_5$ has been published (see R. Strey, R. Schomäker, D. Roux, F. Nallet, V. Olsson, J. Chem. Soc. Faraday Trans., 1990, 86, 2253).

The $C_{12}E_5/H_2O$ system has been studied in detail, in particular by R. Strey et al., J. Chem. Soc. Faraday Trans., 1990, 86, 2253. It produces a lamellar phase up to a water content of 99% by weight within a narrow temperature range. This organised structure is readily evidenced by the fact that the sample appeared birefringing between crossed polarizers, and could be more precisely characterized by measuring radiation diffusion. Thus light diffusion measurements allowed the distance d separating two lamellae to be determined. For a volume fraction f=0.0125 of $C_{12}E_5$, d was of the order of $3 \times 10^7$ m (3000 Å). Further, since the repeat distance between lamellae was of the same order as the wavelength of visible light, the sample illuminated by white light appeared colored due to Bragg reflection.

The phase $L_3$ which appears on the phase diagrams is often termed the abnormal or sponge phase. It may be birefringent on stirring and highly opalescent. Those characteristics are more marked when the solution is diluted. Its structure is defined as a continuous three dimensional bilayer. The bilayers constitute a type of randomly connected network which divides the volume of the solution into two equal parts.

The existence of another phase containing bilayers, the $L_\alpha^+$ phase, has recently been reported by Jonstromer and Strey, J. Phys. Chem., 1992, 96, 5993. It has been observed in surfactants such as $C_{12}E_3$, $C_{12}E_4$, and $C_{14}E_5$, and its exact structure is currently unknown. It has the optical appearance of the $L_3$ phase, i.e., it can be birefringent on stirring in some cases, but it is often more viscous than the $L_3$ phase.

Its zone of existence is completely enclosed in that of the lamellar phase. The borders between the $L_a$ and $L_a^+$ phases are, further, difficult to determine insofar as the relaxation time at the end of which birefringence disappears after stirring has ceased can be relatively long.

The $L_a^+$ phase can currently be defined as a dispersion of bilayers: either in the form of vesicles (simple or multilayered), or in the form of a diphase system in which there is an equilibrium between a lamellar phase and an aqueous phase. The structure remains to be precisely determined.

We have carried out systematic studies, in particular on aqueous compositions containing non ionic surfactants and associative polymers, and surprisingly, we have discovered perfect correlation between the gelling conditions of such systems and those for the appearance of a phase corresponding to bilayers in the phase diagram of the surfactant alone in solution in water.

Our discovery has led us to define a novel process which forms the subject matter of the present invention and, in order to obtain a composition in the form of a gel containing an associative polymer at a given temperature, consists in selecting a surfactant which at that temperature is in the form of bilayers in aqueous solution.

This discovery has also led us to define novel compositions which can be obtained using the process of the invention and in which the surfactant can form liposomes or vesicles.

Thus in a first aspect, the invention provides a process for preparing an aqueous composition in the form of a gel at a given temperature, characterized in that an associative water-soluble polymer constituted by a hydrophilic main chain and hydrophobic pendant groups is brought into the presence, in said composition, of at least one surfactant which is in the form of bilayers when it is in aqueous solution under the same temperature and concentration conditions.

As seen above, some surfactants have been studied in detail as regards their phase diagrams in aqueous solution. For these surfactants, reference is made to the data in the literature in order to determine the conditions in which they are in the form of bilayers. For other surfactants or aqueous media containing components other than the surfactant, which components can modify the phase transition temperature, the phase diagram is determined experimentally in order to determine the conditions under which the surfactants are in the form of bilayers.

The skilled person will, of course, search for birefringence zones which indicate the existence of a bilayer zone before making detailed determinations of the phase diagram.

In order to ensure the presence of bilayers, a radiation diffusion study can be carried out (using light, neutrons, X rays . . . ). Electron microscopy (cryofracture) can also be used to confirm the presence of vesicles and/or liposomes.

In a first variation of the invention, the bilayers form lamellar phases, which may or may not be dispersed.

In the particular case of polyethyleneglycol alkylether type surfactants, in an example in the literature dilute solutions of $C_{12}E_4$ (0.5% to 10%) exhibit separation into two isotropic liquid phases for temperatures in the range 6° C. to 20° C. and separation into a liquid phase and a lamellar phase in the range 20° C. to 50° C. Within that temperature range, gel compositions are formed with that type of surfactant.

When the surfactant is in the form of vesicles, such as liposomes, the gels of the invention are obtained by simple introduction of associative water-soluble polymers into the dispersion of vesicles such as liposomes.

Examples of these surfactants are soya or egg lecithin, saturated or unsaturated monoalkylethers of polyethyleneglycol or linear or branched polyglycerol, or any other ionic or non ionic surfactant which can form vesicles.

The associative polymers used in the process of the invention are all the associative polymers cited above.

The hydrophilic main chain of these polymers can, in particular, result from polymerisation of a hydrophilic monomer containing functions onto which hydrophobic chains can subsequently be grafted, for example acid functions.

This method of preparing associative polymers is described in particular in the Shalaby W. Shalaby publication cited above, which publication is incorporated in its entirety by reference.

A water-soluble polymer of natural origin, or a natural polymer rendered water-soluble by chemical modification, can also be used.

Associative polymers can also be formed by copolymerisation of hydrophilic monomers and hydrophobic monomers. These hydrophobic polymers, introduced into the reaction medium in a much smaller quantity than the hydrophilic polymers, generally comprise a fatty hydrocarbon chain. This method of preparation is described in the publication by S. Biggs et. al., J. Phys Chem. (1992, 96. pp 1505–11).

Examples of these polymers are acrylic polymers, polyethers, and polyosidic chains which may be partially substituted.

The hydrophilic main chain is constituted as described above by a succession of hydrophilic monomer units and a fraction of monomers carrying highly hydrophobic pendant groups.

The molar percentage of monomers carrying hydrophobic pendant groups is termed the modification percentage of the hydrophilic chain.

This degree is activity in the range 0.1% to 10%, preferably in the range 0.5% to 5%, and more preferably in the range 1% to 3%.

The hydrophobic pendant groups can be any hydrophobic pendant group which is conventionally used to prepare associative polymers. Preferably, the hydrophobic groups used comprise a backbone containing at least 8 carbon atoms, preferably 12 to 18 carbon atoms.

Particular examples of these hydrophobic groups are linear, branched, saturated or unsaturated hydrocarbon chains which may or may not contain cycles.

Preferred examples of hydrophobic groups are hydrocarbon chains, in particular alkyl chains, containing 8 to 28 carbon atoms, preferably 12 to 18 carbon atoms.

Modified units are advantageously in the form of an ether, ester or amide. This is particularly the case when the main chain of the associative polymer is an acrylic chain.

The associative polymers used in the process of the invention can have a mass average molar mass in the range $10^4$ to $10^7$, preferably in the range $10^5$ to $10^6$.

The concentration of associative polymer in the aqueous composition is generally in the range 0.5% to 10% by weight, when the polymer has a mass average molar mass of the order of 150000. This concentration can, of course, be lower for a polymer with a larger average molar mass.

The surfactant can be any surfactant which can form bilayers at the temperature and under the conditions for preparing the gel.

It may be a non ionic surfactant, for example a polyethyleneglycol monoalkylether with general formula:

$$C_iH_{2i+1}(OCH_2CH_2)_jOH$$

which is symbolically represented as $C_iE_j$.

Preferably, i is in the range 8 to 18, more preferably 12 to 14, and j is in the range 1 to 10, preferably 3 to 5.

Surfactant $C_{12}E_4$ is of particular interest due to its thermal behavior.

It may also be a non ionic surfactant with general formula:

$$C_iH_{2i-1}(OCH_2CH_2)_jOH$$

which is a polyethyleneglycol monoalkylether in which the alkyl chain contains one unsaturation. In this case, i is preferably in the range 12 to 24, more preferably i is 18; and j is in the range 1 to 20, preferably 10.

We may also have a polyglycerol monoalkylether, in particular with formula:

$$R^0O-[C_3H_5(OH)O-]_n-H$$

in which:

i) $C_3H_5(OH)O$ is one of the following structures, taken as a mixture or separately:

$$-CH_2CHOHCH_2O-\ ;\ -CH_2-\underset{CH_2OH}{\overset{|}{C}HO}-\ ;$$

$$-\underset{CH_2OH}{\overset{|}{C}H}-CH_2O-\ ;$$

ii) n is an average statistical value in the range 1 to 6;
iii) $R^0$ represents:
  a) a linear or branched, saturated or unsaturated aliphatic chain containing 12 to 30 carbon atoms; or a hydrocarbon-containing radical of a lanoline alcohol; or the residue of a long-chain α-diol;
  b) an $R^1CO$ residue, where $R^1$ is a linear or branched aliphatic $C_{11}$–$C_{17}$ radical;
  c) an $R^2$—[$OC_2H_3(R^3)$—] residue, where:
    $R^2$ has the meaning given in a) or b) for $R^0$;
    $OC_2H_3(R^3)$— is one of the following structures, taken as a mixture or separately:

$$-\underset{R^3}{\overset{|}{O}CH}-CH_2-\quad \text{and} \quad -O-CH_2-\underset{R^3}{\overset{|}{C}H}-$$

where $R^3$ has the meaning given in a) for $R^0$; or it may be a linear or branched ether of polyglycerol containing two fatty chains.

The surfactant can also be an ionic surfactant.

Examples are soaps such as sodium oleate, lecithin such as soya or egg lecithin, quaternary ammonium derivatives such as dialkyldimethylammonium type compounds, the alkyl group being a fatty chain containing at least 8 carbon atoms. A particular example is dioctadecyldimethylammonium bromide.

One class of surfactants which is of particular interest to the invention is constituted by those which can form liposomes. Examples of these surfactants are phospholipids, and soya or egg lecithin.

In an advantageous variation of the invention, the aqueous compositions contain 0.1% to 20%, preferably 0.1% to 10% by weight of surfactant or of a mixture of surfactants.

In order to control bilayer formation, it may be of interest to use a mixture of surfactants rather than one surfactant, in particular a mixture of surfactants of the type $C_iE_j$. Such a mixture allows the hydrophobic nature of the system to be adjusted at will. Thus, for example, by progressively replacing $C_{12}E_5$ with $C_{12}E_3$, keeping the total concentration of the surfactant constant, the apparent hydrophobic nature of the water—surfactant mixture can be increased with the result that the temperatures corresponding to the different phase transitions are continuously reduced.

Thus the use of such mixtures can allow the phase transition temperatures of water—surfactant mixtures to be varied and as a result, the temperature at which a gel appears in the presence of an associative polymer can be varied.

An analogous result can be obtained by introducing a fatty alcohol into the composition to modify the phase transition temperature. An example of a fatty alcohol which can be used for this purpose is hexanol. The concentration is advantageously 0.1% to 2%.

Other substances can also be used to control bilayer formation. Particular examples are sterols, fatty alcohol or sterol phosphates, fatty alcohol or sterol sulfates, fatty acids, fatty amines, saponins, triterpene derivatives, ceramides, and sphingosines.

Depending on the nature of the surfactant, the process of the invention can be used:

either to prepare a composition containing an associative water-soluble polymer which is fluid at a relatively low temperature and which gels within a higher range of temperatures, which is the case for surfactants in which the phase diagram exhibits a lamellar phase in this temperature range, while it has a biphase zone at a lower temperature. Thus the invention provides a process for preparing a composition containing an associative water-soluble polymer which is fluid at a given temperature termed the lower temperature and which gels within a range of temperatures which is higher than said temperature, the process consisting in introducing a surfactant into said composition, said surfactant having a phase diagram which exhibits a lamellar phase zone in said range of temperatures and a biphase zone at the lower temperature;

or to gel a dispersion of vesicles, in particular liposomes, by introducing an associative polymer into said dispersion.

As seen above, the process of the invention provides a means of considerably varying the viscosity of an aqueous composition containing an associative polymer by introducing a surfactant into the composition and by selecting the conditions such that the surfactant is in the form of bilayers.

This process for increasing the viscosity of an aqueous composition has a particularly important application in stabilising aqueous suspensions of particles, particularly in stabilising suspensions used in cosmetics, paints, or food additives.

Thus in a further aspect, the invention concerns the application of the process described above to stabilising an aqueous suspension of liquid or solid particles.

Examples of suspensions of solid particles which can be stabilised using the process of the invention are any suspensions of particles with a dimension in the range 0.02 microns to 50 microns, more particularly suspensions of pigments, talcs, or micas. These particles may have been surface treated.

Particular examples of suspensions of liquid particles are emulsions, more particularly emulsions of droplets with dimensions in the range 0.05 microns to 10 microns, for example oil-in-water emulsions.

Examples of other suspensions of particles of the invention are dispersions which are organised in the form of bilayers such as lamellar phases, vesicles, or liposomes.

A particularly interesting use for the process of the invention is transforming a suspension of liposomes into a gel by introducing an associative water-soluble polymer into said suspension. The invention thus provides a means of stabilising a liposome suspension at any temperature.

Such liposome suspensions with increased viscosity constitute novel compositions and thus the invention also provides, as novel substances, compositions containing liposomes and an associative water-soluble polymer.

Other aims, features and advantages of the invention become clear from the following description which refers to a number of examples of preferred implementations which are given simply by way of illustration and which in no way limit the scope of the invention. In the examples, all the percentages are given by weight unless indicated otherwise.

BRIEF DESCRIPTION OF THE DRAWINGS

The invention is further described by reference to the accompanying drawings in which.

EXAMPLES

Example 1

Modified acrylic polymers were prepared with the following structures:

where x is the modification percentage in mole % and n is the number of carbon atoms in the alkyl chain. The modified acrylic polymers were prepared from polyacrylic acid (PAA) with a mass average molar mass of 150000. The modified derivatives were prepared using the procedure described By T. K. Wang, I. Iliopoulos, R. Audebert, Polym. Bull. 1988, 20, 577. Modified polymers are designated x-$C_n$ below (for example 1-$C_{18}$ designates a modified polyacrylate containing 1 mole % of N-octadecylacrylamide units). The modified polymers had the same degree of polymerisation as the PAA precursor and a statistical distribution of alkyl groups along the chain.

The surfactants ($C_{12}E_4$, $C_{12}E_5$, $C_{12}E_3$) used to prepare the compositions were monododecylethers of oligoethyleneglycol with a purity of more than 98%.

a) Preparation of Polymer/Surfactant Mixtures

The mixtures studied were prepared by mixing intermediate solutions of polymer and of surfactant containing double their concentration in the final mixture, and were obtained after 24 hours of stirring.

$C_{12}E_4$ solutions were prepared at a sufficiently low temperature for the solution to be isotropic.

b) Monitoring of Viscosity

Measurements were carried out using a Carri Med controlled stress rheometer or, for solutions with low viscosities, a Low-Shear 30" apparatus from Contraves.

c) Determination of Gel Formation: Thermal Gelling

Figure 1:
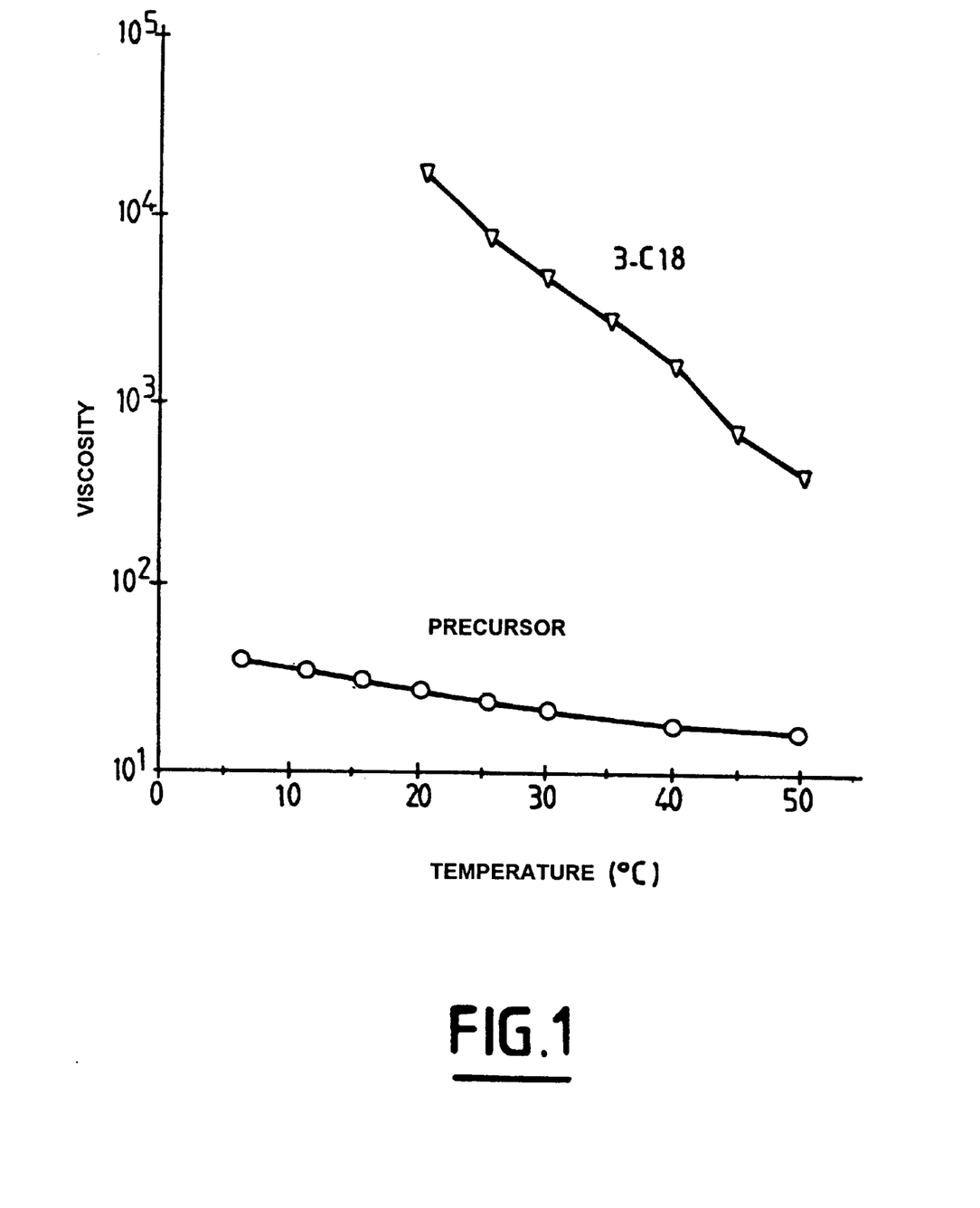
FIG. 1 shows curves of a 2% solution of precursors and of a modified 3-$C_{18}$ polymer in which the ordinate shows the viscosity expressed in Pa.s., and the abscissa shows the temperature in ° C.

In general, the viscosity and/or elastic modulus of solutions of polymers decreases with increasing temperature. A typical example of such an effect is given for comparison in FIG. 1 which shows the viscosity of a 2% solution of precursor and modified polymer 3-$C_{18}$ as a function of temperature. Very different behavior was observed with mixtures of modified acrylic polymers and $C_{12}E_4$ and for concentrations of surfactants of more than $10^{-2}$ mol/l.

Figure 2:
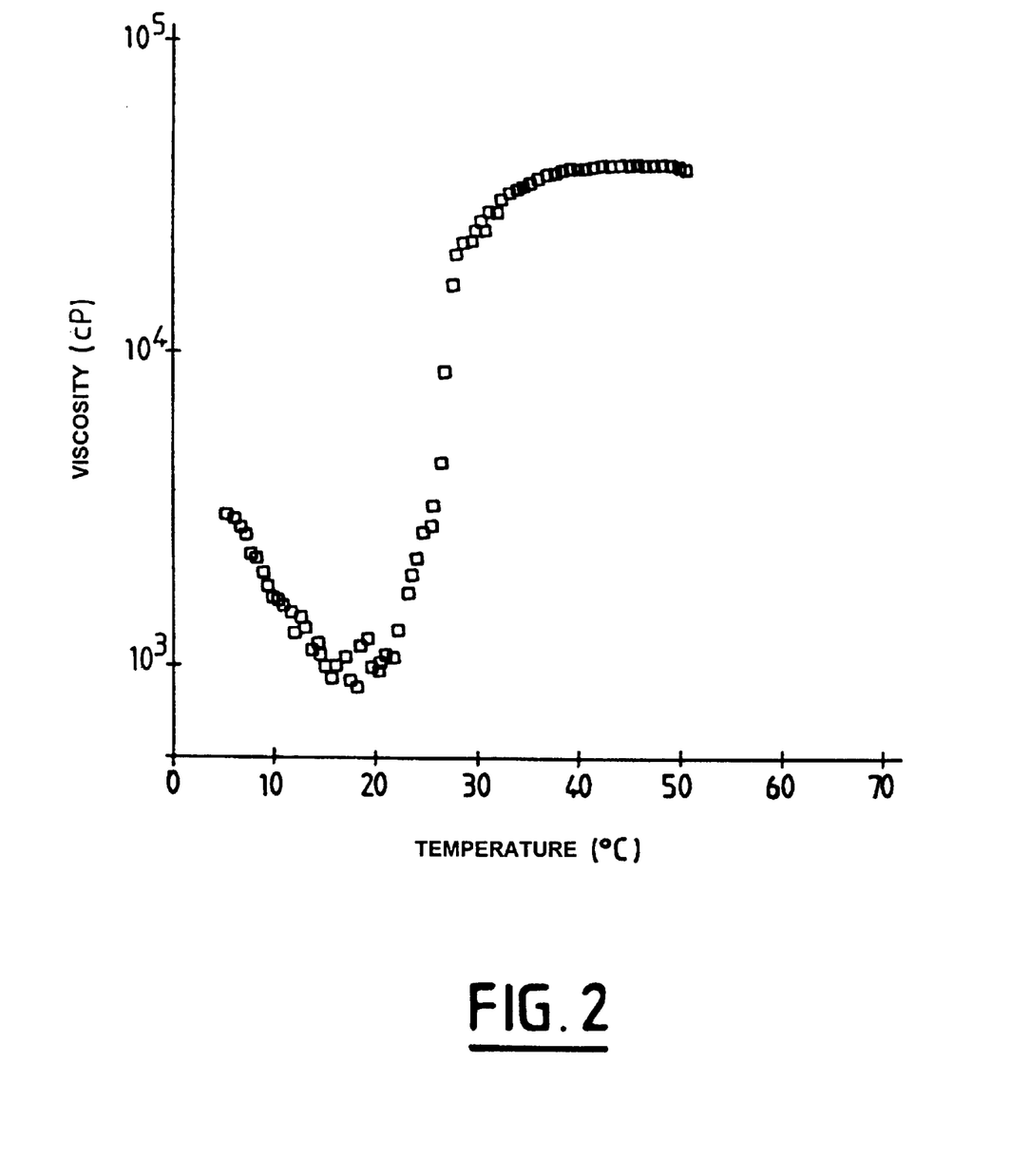
FIG. 2 shows a curve similar to FIG. 1 showing the viscosity of a mixture of polymer 3-$C_{12}$ and surfactant $C_{12}E_4$.

FIG. 2 shows the viscosity of mixtures of 3-$C_{12}$ and $C_{12}E_4$ as a function of temperature for a surfactant concentration of 0.1 mole per liter and a polymer concentration of 1% by weight. Very substantial variations can be seen in the range 20° C. to 30° C.

The viscosity can vary greatly in this zone depending on the concentration of surfactant.

The change in the rheological behavior of the water/surfactant/polymer system corresponds to the observed phase transition for the binary surfactant/water system: this system passed from two liquid isotropic phases at a temperature of less than 20° C. to a lamellar dispersion in water at a temperature of more than 20° C. (see D. J. Mitchell, G. J. T. Tiddy, L. Waring, T. Bostock, M. P. McDonald, J. Chem. Soc. Faraday Trans. 1, 1981, 79, 975).

Example 2

Sample solutions were prepared containing mixtures of $C_{12}E_4$ and $C_{12}E_5$ in various proportions, along with a solution of PAA 1-$C_{18}$ polymer with a mass average molar mass of 150000, hereinafter termed PAA-150-1-$C_{18}$. The concentration was double that of the final solution obtained after mixing, such that in the final composition, the surfactant mixture concentration was 2% by weight of non ionic surfactant and the polymer composition concentration was 1% by weight of polymer.

Figure 3:
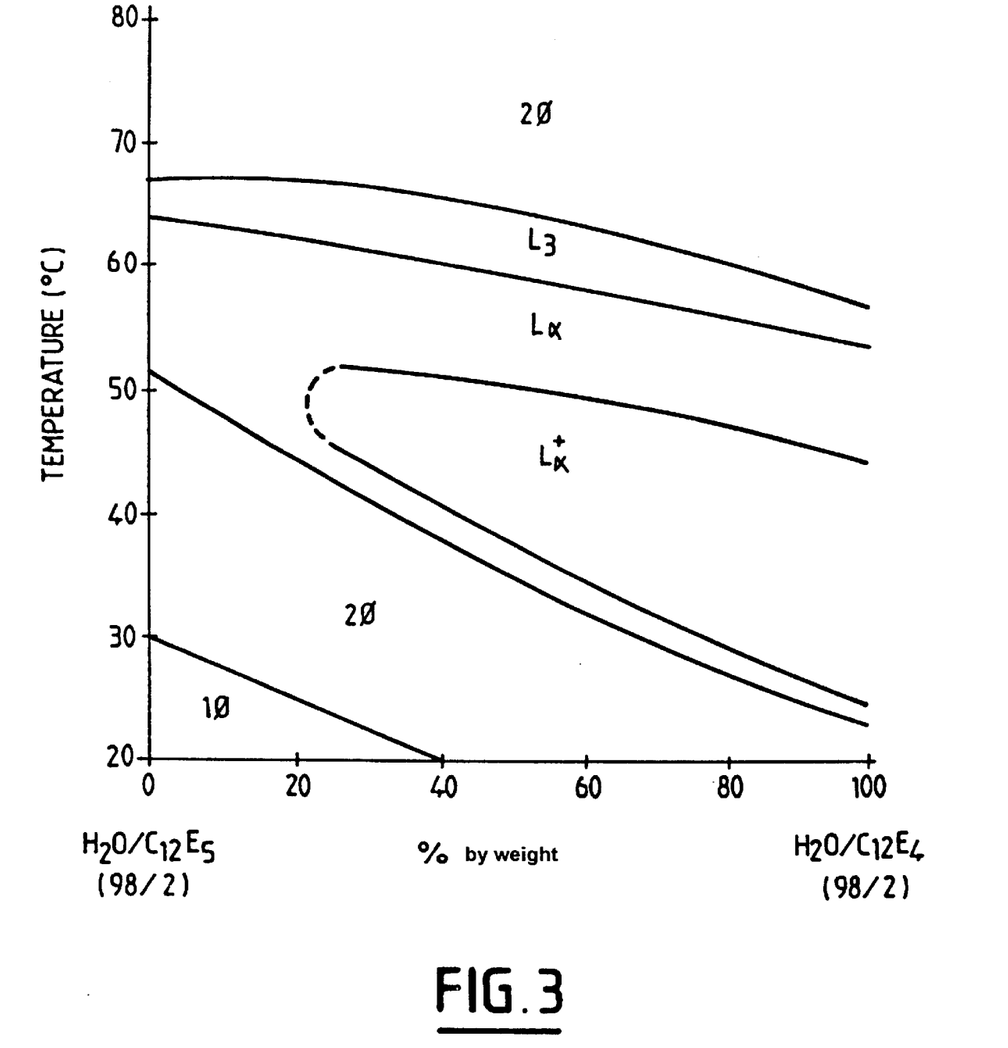
FIG. 3 shows the phase diagram of a water—surfactant mixture $H_2O/C_{12}E_5$ (in relative proportions of 98/2 by weight) and water—surfactant $H_2O/C_{12}E_4$ (in relative proportions of 98/2 by weight); along the abscissa are the variable relative proportions by weight from 0% of $H_2O/C_{12}E_4$, i.e., 100% of $H_2O/C_{12}E_5$, to 100% of $H_2O/C_{12}E_4$, i.e., 0% of $H_2O/C_{12}E_5$; the temperature in ° C. is up the ordinate.

On progressive replacement of $C_{12}E_5$ by $C_{12}E_4$ in this mixture, a single pseudo surfactant was prepared in which the cloud temperature gradually reduced as the $C_{12}E_4$ became the major constituent. This resulted in a progressive increase in the hydrophobic nature of the pseudo surfactant as shown in FIG. 3.

Further, the transition temperature $2\Phi\text{-}L_a$ also reduced regularly as the proportion of $C_{12}E_4$ increased. Thus this transition temperature could be controlled as it is governed by the composition of the $C_{12}E_4/C_{12}E_5$ mixture.

Figure 4:
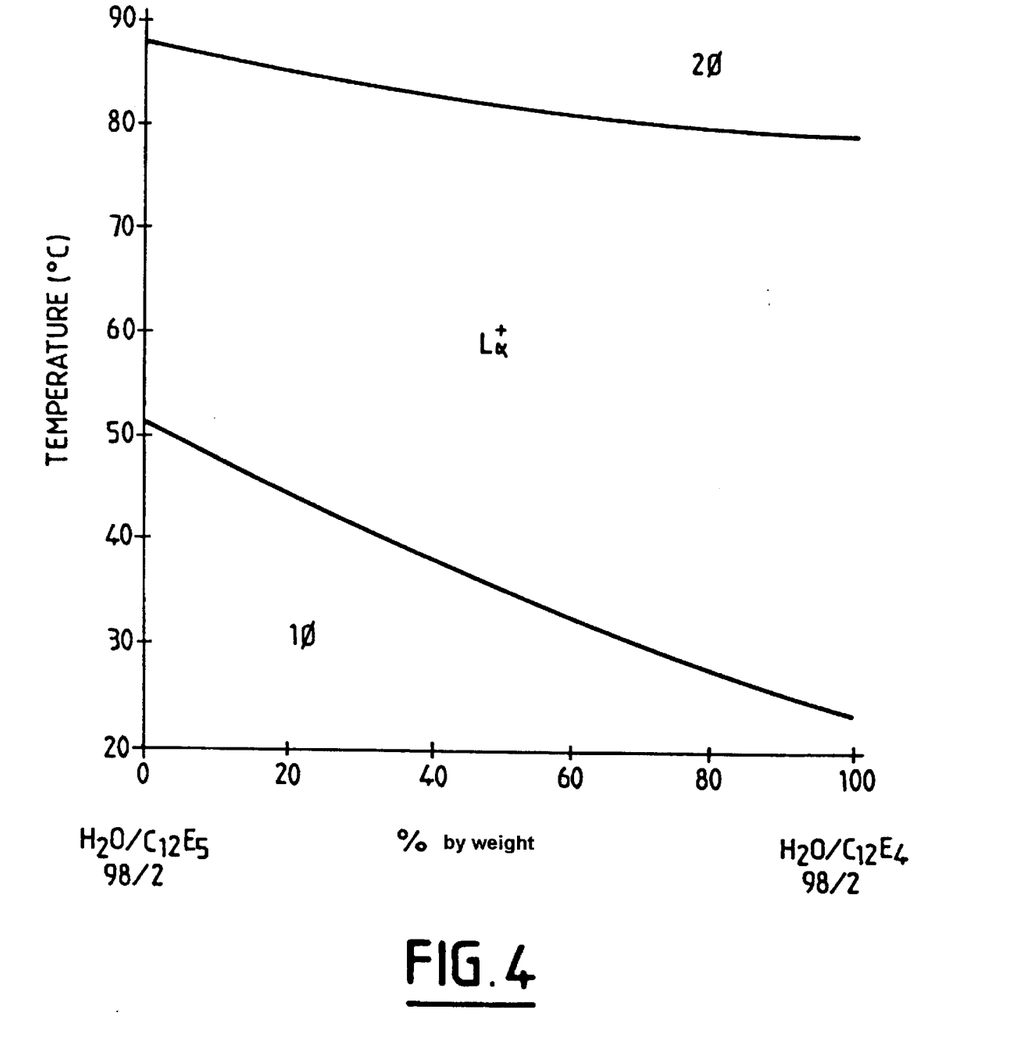
FIG. 4 shows the phase transition diagram derived from FIG. 3 by addition of 1% by weight of PAA-150-1-$C_{18}$ to the solution.

FIG. 4 shows the phase diagram of the same system in the presence of PAA-150-1-$C_{18}$. It can be seen that the addition of PAA-150-1-$C_{18}$, at 1% by weight in the solution, considerably modified the phase diagram: the diphase zone disappeared to the advantage of a large, clear, monophase isotropic zone. As the temperature increased, the samples became birefringent on stirring alone, which appears to indicate the appearance of a $L_a^+$ zone.

The perfect similarity between the border separating the diphase zone from the zone in which the lamellar zone exists in the case of surfactants alone in water and that separating the isotropic uniphase zone from the zone in which the $L_a^+$ exists in the presence of the polymer is quite remarkable.

Example 3

Five samples a, b, c, d and e were prepared containing 2% of surfactant constituted by surfactants $C_{12}E_4$, $C_{12}E_3$ and $C_{12}E_5$ in the proportions shown in Table 1 and 1% of polymer 1-$C_{18}$ constituted by polyacrylic acid with a mass average molar mass of 150000 modified with 1 mole % of an octadecyl chain.

For each mixture a to e, the temperature $T_L$ was determined at which the water/surfactant system underwent a phase transition, the isotropic phase/phase containing vesicle transition: this temperature $T_L$ is shown in Table 1 below.

a) Viscosity Evolution Study

Figure 5:
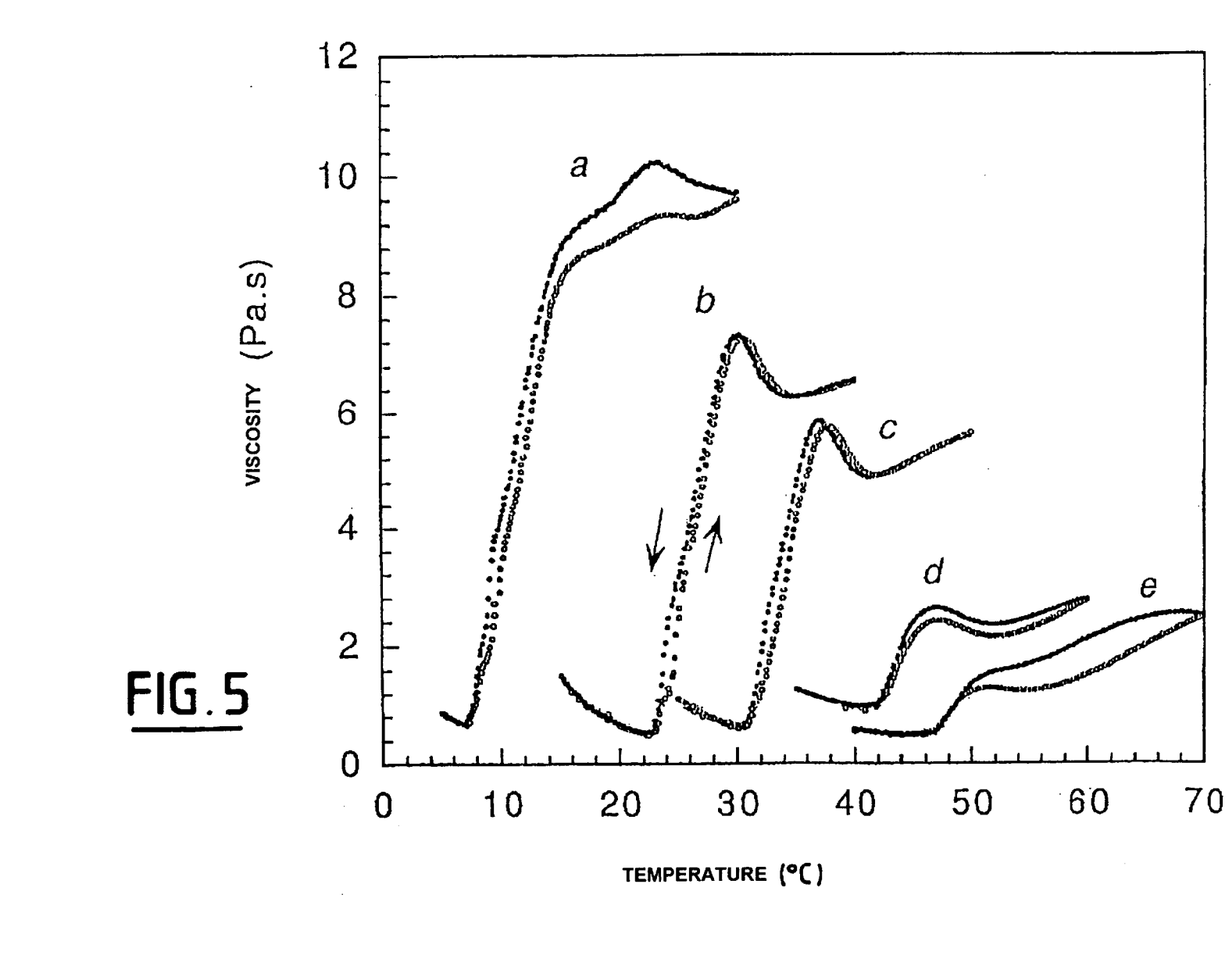
FIG. 5 shows the variations in the viscosity with temperature of the different mixtures a to e in Example 3.

For each mixture the curve giving the viscosity of the ternary mixture (or quasi-ternary mixture when the surfactant is a mixture of surfactants) of surfactant/1-$C_{18}$/water was recorded using a Carri med controlled stress rheometer with a 4 cm diameter cone and a 2° angle with a speed gradient of $10\ s^{-1}$ and a temperature variation of 0.5° C. per minute. FIG. 5 shows these curves of variations in the viscosity of the different mixtures with increasing and decreasing temperature.

The gel temperatures $T_G$ of the different systems, determined from the curves of FIG. 5, are shown in Table 1 below.

TABLE 1

| Curve | Composition | Phase transition temperature $T_L$ | Gel temperature $T_G$ |
|---|---|---|---|
| a | $C_{12}E_4$ 56.5% $C_{12}E_3$ 43.5% | 7.5° C. | 7.5° C. |
| b | $C_{12}E_4$ | 23° C. | 23° C. |
| c | $C_{12}E_4$ 65.8% $C_{12}E_5$ 34.2% | 32° C. | 31.5° C. |
| d | $C_{12}E_4$ 25.6% $C_{12}E_5$ 74.4% | 42° C. | 42° C. |
| e | $C_{12}E_5$ | 51° C. | 48° C. | b) Flow Curve Study

For each of the above samples, flow curves representing variations in viscosity as a function of the velocity gradient were recorded at different temperatures using a Rheometrics apparatus which carried out logarithmic sweeps of the rising and falling velocity gradient (also known as thixotropic loops) from $0.1\ s^{-1}$ to $100\ s^{-1}$. Two sweep rates were used:

increase and decrease of gradient each carried out over 14 minutes, separated by a plateau of 30 second's duration at $100\ s^{-1}$;

increase and decrease of gradient each carried out over one hour, separated by a plateau of 1 minute's duration at $100\ s^{-1}$.

A clear modification in the shape of these flow curves was observed when the phase transition temperature was crossed.

c) Oscillation Study

The above samples were studied dynamically using a Rheometrics apparatus which applied a sinusoidal deformation with an amplitude which was set by the operator which simultaneously measured the sinusoidal strain which resulted and deduced, following calculation, the values of the elastic modulus G' and the loss modulus G".

All the samples studied had substantially the same linear region which extended from 0% to 100% deformation. In order to compare them, they were subjected to a sinusoidal deformation of 8% amplitude and the evolution of G' and G" was studied over a frequency range of 0.015 Hz to 15 Hz, at different temperatures.

Each sample was subjected to the following protocol:

measurement of G' and G" without preshearing;

measurement of G' and G" after applying a velocity gradient of $10\ s^{-1}$ for 10 seconds to the sample;

measurement of G' and G" after applying a velocity gradient of $30\ s^{-1}$ for 10 seconds to the sample;

measurement of G' and G" after applying a velocity gradient of $50\ s^{-1}$ for 10 seconds to the sample;

measurement of G' and G" after applying a velocity gradient of $30\ s^{-1}$ for 30 seconds to the sample.

The results obtained show that at a temperature above $T_G$, the evolution of the moduli as a function of frequency varied little from one sample to another. This similitude on the macroscopic level is probably connected to an analogy in the microscopic structure. The values of the moduli depended on the surfactants contained in the solution.

Before the transition, the shape of the modulus curves depended little on the sample under consideration: a straight line with a slope of close to 2 for G' and a straight line with a slope of close to 1 for G". Further, the straight lines were superimposable by simple translation along the frequency axis.

Example 4

Determination of Variations in Viscosity with Temperature

Figure 6:
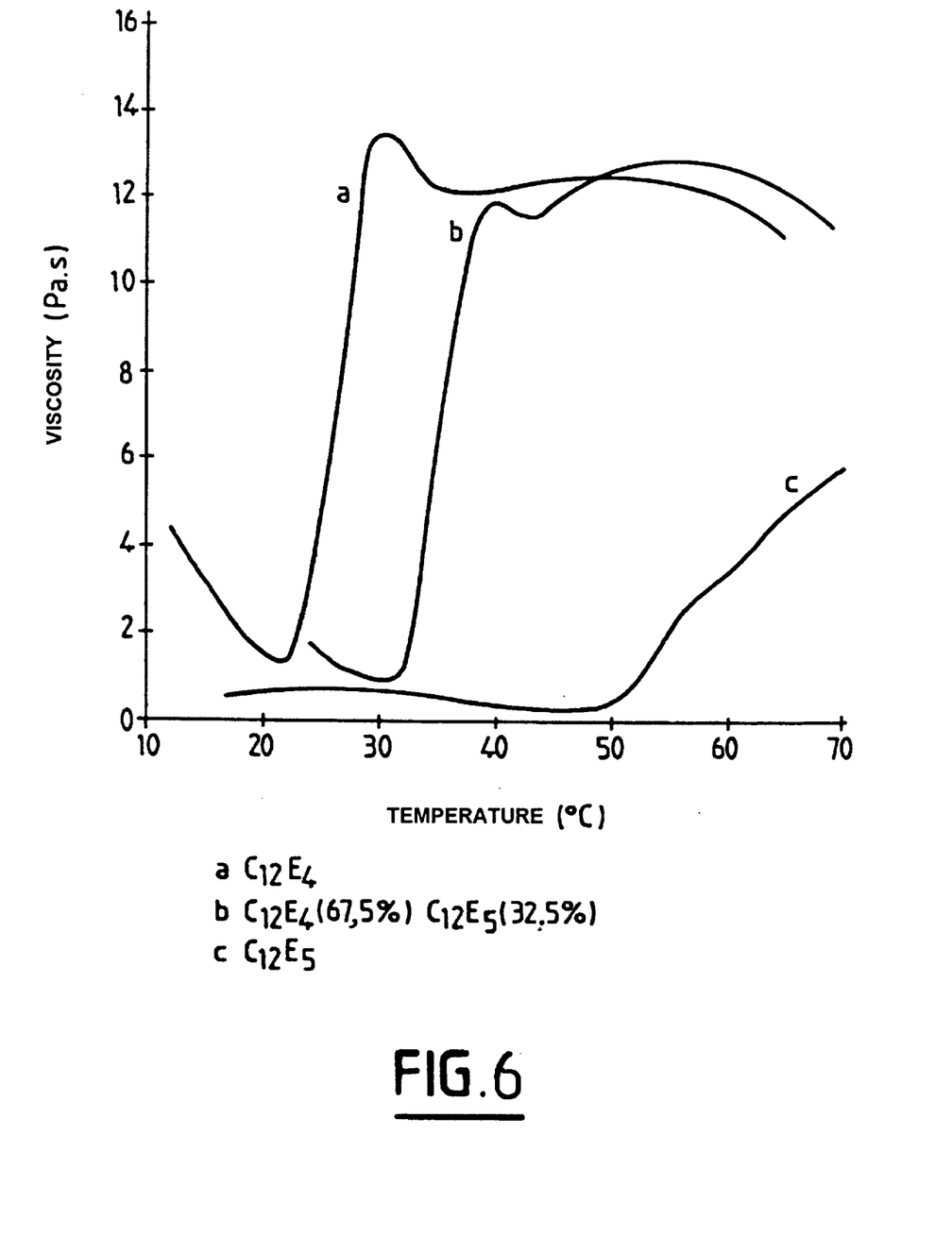
FIG. 6 shows the variations in viscosity up the ordinate in Pa.s. as a function of temperature in ° C. along the abscissa for three mixtures described in Example 4 with three different surfactants. Curve a is with surfactant $C_{12}E_{14}$, curve b is for a mixture of 67.5% of $C_{12}E_4$ and 32.5% of $C_{12}E_5$, and curve c is for the surfactant $C_{12}E_5$.

FIG. 6 shows the variations in the viscosity in Pa.s. with temperature in ° C. for a solution of 1% modified polyacrylic acid, termed PAA-150-1-$C_{18}$ defined in Example 2, and different surfactants or surfactant mixtures at a total concentration of 2% by weight of surfactant.

Curves a, b and c of FIG. 6 respectively correspond to the following surfactants:

$C_{12}E_4$ for curve a;

a mixture of 67.5% of $C_{12}E_4$ and 32.5% of $C_{12}E_5$ for curve b;

$C_{12}E_5$ for curve c.

An increase in viscosity was observed at the transition temperature between the isotropic phase and the $L_a^+$ phase of the surfactant/polymer mixture. This increase was sharp and large (apparent viscosity multiplied by 10) for samples containing exclusively and mostly $C_{12}E_4$. The observed phenomenon was slightly different for samples containing exclusively and mainly $C_{12}E_5$: the increase in viscosity was more gradual and smaller (viscosity multiplied by a factor of the order of 5).

This phenomenon was reproducible as regards the temperature at which the viscosity modification appeared, when the experiment was repeated, for an increase and a decrease in temperature.

Example 5

Mixtures Containing 4% of Surfactants and 1% of Polymer 1-$C_{18}$

As in Example 3, the Theological behavior of solutions containing 4% of $C_{12}E_4$ and 1% of polymer 1-$C_{18}$ was studied by tracing the thixotropic loops at different temperatures and examining the evolution of the moduli as a function of frequency.
a) Flow Curves Before the phase transition, the viscosity of the sample hardly varied with velocity gradient and was lower (by about one order of magnitude) than the viscosity of the solution containing 2% of $C_{12}E_4$ and 1% 1-$C_{18}$ solution under the same conditions.

After the transition, the viscosity reduced regularly with the velocity gradient, but had higher values than those of the 2% $C_{12}E_4$ solution.

In the solution containing 4% of $C_{12}E_4$, before the transition temperature, the micelles were more numerous than in the 2% solution. The aggregate/macromolecular chain ratio was increased. This allowed a reduction in associations between macromolecules which could persist in the 2% surfactant solution.

Beyond the transition temperature $T_G$, the higher concentration of surfactant resulted in an increase in the number and size of the vesicles. This led to a higher number of bridges between chains.
b) Oscillation Study Analogous behavior to that of solutions containing 2% of non ionic surfactant and 1% of polymer was observed.

Below the phase transition, the elastic modulus G' was less than the loss modulus G". In logarithmic coordinates, the curves representing G' and G" were straight lines with slopes of about 1 and, at the same frequency, their values were lower than those of the 2% $C_{12}E_4$ and 1% polymer solution. Above the transition, the elastic modulus became greater than the loss modulus and the two varied little with frequency.
c) Influence of an Addition of 30% by Weight of Glycerine The rheological behavior was unchanged. Only the transition temperature changed and the viscosity was slightly increased.

Example 6

Mixture Containing 10% of Surfactant and Polymer 1-$C_{18}$ a) Study of Viscosity Evolution of as a Function of Temperature As in example 3, several successive temperature rises and falls were carried out at a rate of 0.5° C. per minute, at a velocity gradient of 10 s$^{-1}$, using compositions containing 1%, 2%, 3% and 5% of polymer 1-$C_{18}$ and 10% of $C_{12}E_4$.

The viscosity increase always occurred at the same temperature (23° C.±1° C.) which was the phase transition temperature (micellar phase to phase containing bilayers).

These systems reached their equilibrium state more slowly than samples containing only 2% of surfactant.
b) Oscillation Study Above the transition temperature, the samples behaved elastically: the elastic modulus G' and the loss modulus G" varied little with frequency and G' was higher than G".
c) Influence of Addition of 30% of Glycerine As with the samples containing 4% of $C_{12}E_4$, the behavior of the solutions was not modified; only the phase transition temperatures were modified.

Example 7

Composition Containing Liposomes

A suspension of liposomes in water was prepared from

4% of soya lecithin (Alcolec F100)

96% of water.

The mixture was homogenised using ultrasound for 15 minutes at 4° C. at a power of 150 watts.

A suspension of liposomes with a viscosity of close to that of water was obtained.

An equal volume of a solution of associative polymer PAA-150-3-$C_{18}$ constituted by polyacrylic acid with an average molar mass of 150000 containing 3 mole % of N-octadecylacrylamide units at concentrations of 1% and 2% by weight was introduced into this liposome suspension.

In both cases, a very substantial increase in viscosity was observed.

Example 8

Composition Containing Liposomes

An aqueous suspension containing 2% by weight of liposomes obtained from soya lecithin and β-sitosterol in a ratio of 9/1 by weight was prepared.

As in the previous case, an equal volume of 1% to 2% of PAA-150-3-$C_{18}$ was added: in the two cases, gel formation was observed.

Example 9

Composition Containing Liposomes

Three suspensions A, B and C of liposomes were prepared, containing respectively 3%, 2% and 1% of soya lecithin (Alcolec F100).

The solutions obtained were then microfluidized. The particle size was determined by examining the samples using an electron microscope after cryofracture: it varied over the range 50 nm to 500 nm.

Addition of polymer 1-$C_{18}$ to these solutions caused an increase in the viscosity as a function of the respective concentrations of phospholipids and polymer. Whatever the temperature under consideration, the phospholipids organised themselves into bilayers. The parameter which determined the rheological behavior of the solutions was no longer the temperature, but the respective concentrations of phospholipids and 1-$C_{18}$ polymer, and the ratio between the two concentrations.

Figure 7:
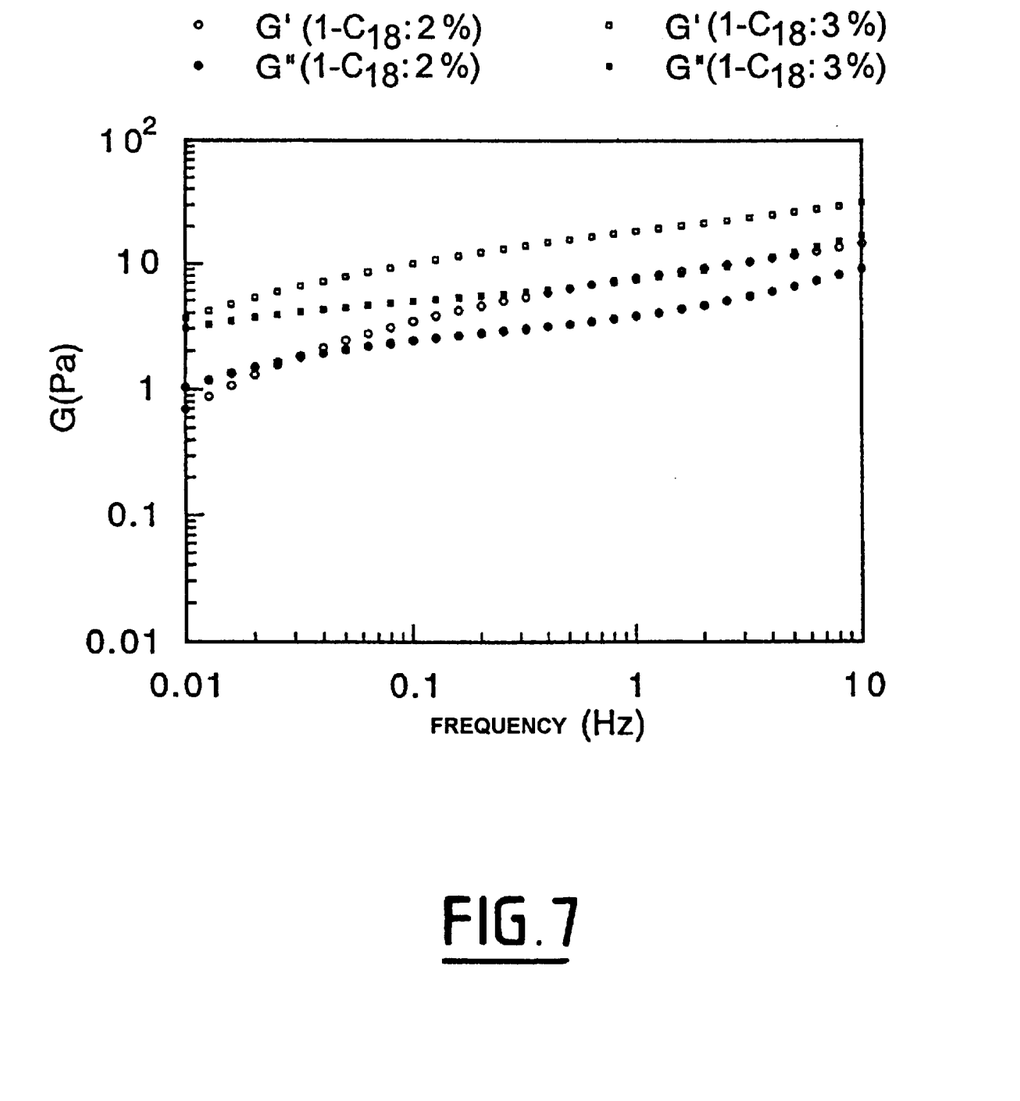
FIGS. 7, 8 and 9 show the evolution of the elastic modulus G' and the loss modulus G" for compositions containing respectively 3%, 2% and 1% of soya lecithin and different concentrations of polymer 1-$C_{18}$.
Figure 8:
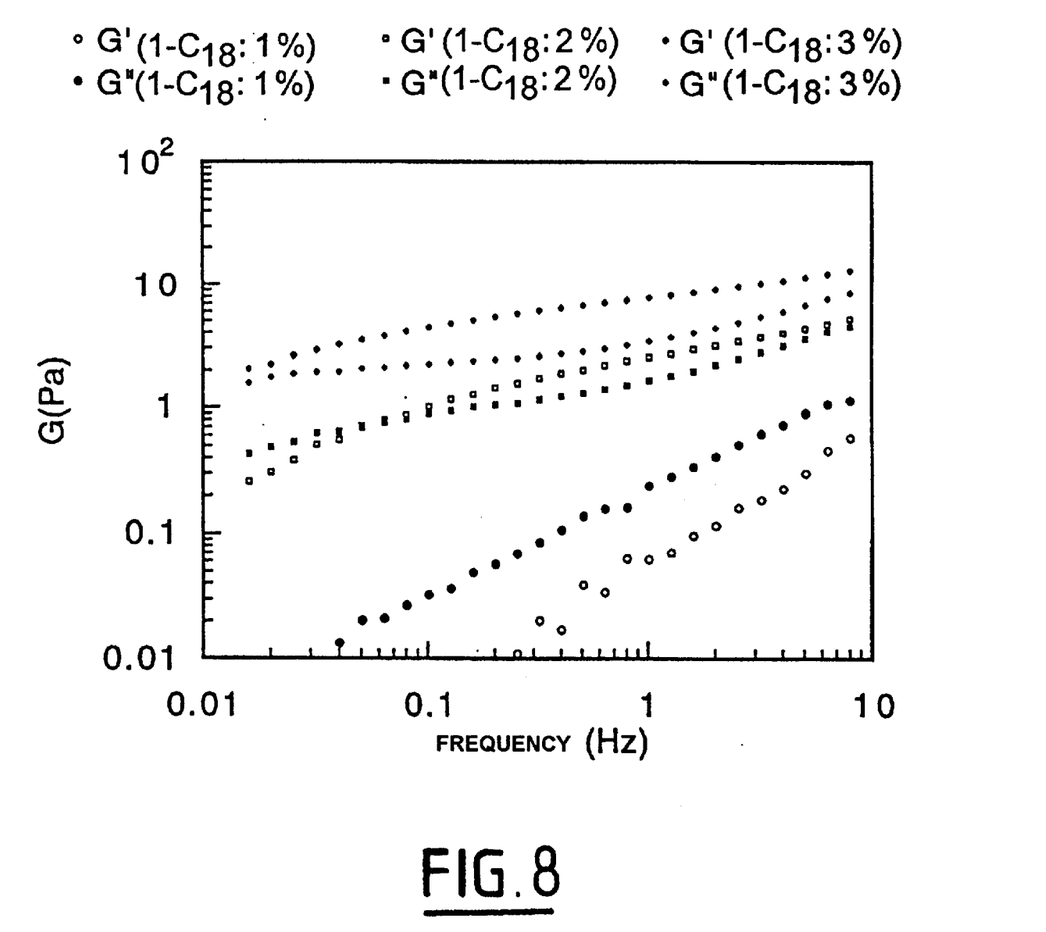
Figure 9:
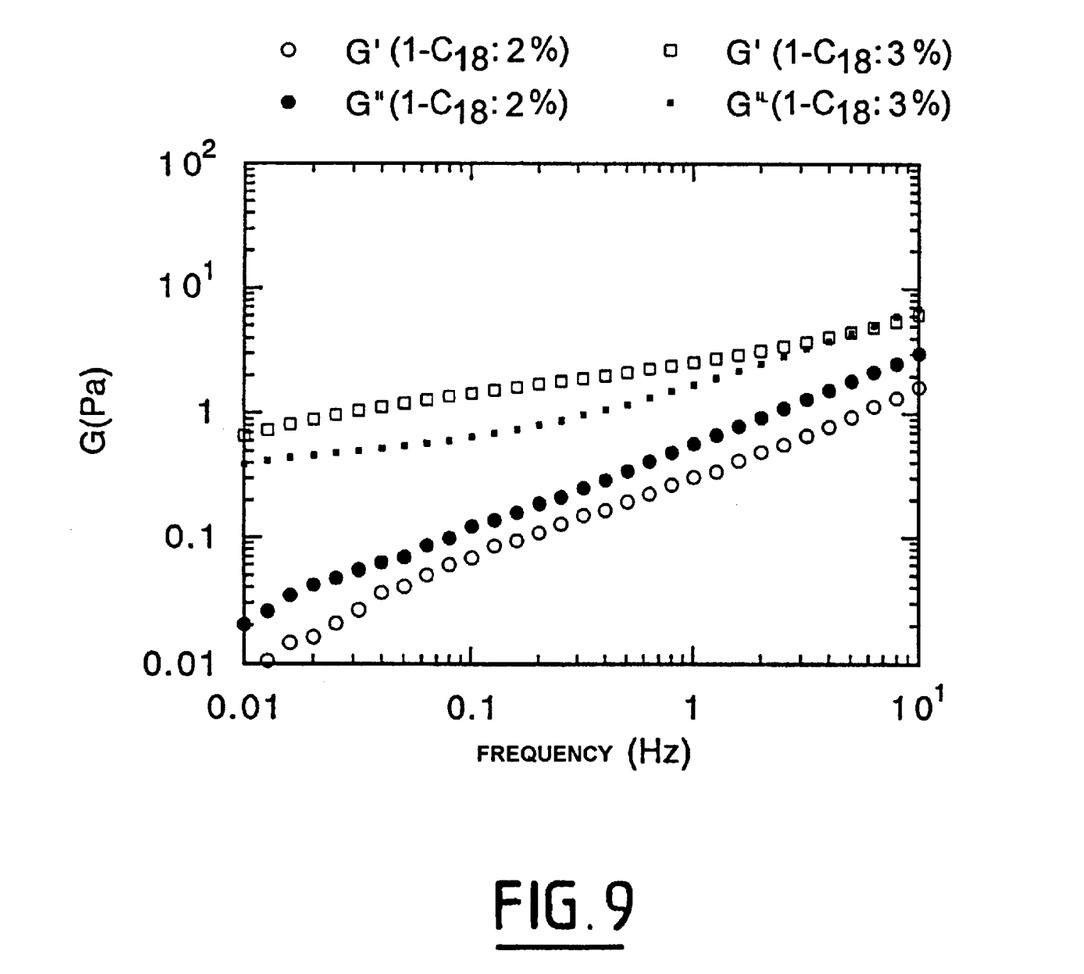

The evolution of the elastic modulus G' and loss modulus G" of the Alcolec solution was studied as a function of the respective concentrations of phospholipids and 1-$C_{18}$ polymer. The results are shown in the curves of FIGS. 7, 8 and 9 which show the evolution of moduli G' and G" for the compositions A, B and C as a function of frequency for the different concentrations of 1-$C_{18}$.

Example 10

Composition Containing Non Ionic Lipid Vesicles

A suspension was prepared in water of non ionic lipid vesicles constituted by polyethyleneglycol octadecylether with formula $$CH_3(CH_2)_7CH=CH(CH_2)_7CH_2(OCH_2CH_2)_nOH$$

which is commercially available under the trade name Brij 96-A7606. 4% by weight of this surfactant was introduced into the water and the mixture was heated to 50° C. with stirring, then cooled to room temperature.

This suspension was mixed in 1/1 proportions with a 2% by weight solution of the associative polymer designated PAA-150-3-$C_{18}$.

A substantial increase in viscosity was observed, along with gel formation.

The invention also concerns all means constituting techniques equivalent to the means described and combinations thereof. Further, the invention also protects any feature in the description taken as a whole which appears to be novel over any prior art.

What is claimed is:

1. A process for preparing a gel from an aqueous suspension of liquid or solid particles at a selected temperature, comprising:
   (a) selecting at least one surfactant at a concentration of about 0.1 to 10% by weight, such that said surfactant at said concentration form bilayers in an aqueous composition at said selected temperature;
   (b) forming an aqueous suspension of liquid or solid particles with said surfactant;
   (c) adding to said suspension an effective amount of a water-soluble associative polymer, said associative polymer having a mass average molar mass of about $10^4$ to about $10^7$, and comprising a hydrophilic polymer having intermittent side chains comprising hydrophobic groups containing at least 8 carbon atoms, said amount of associative polymer being effective to cause said suspension to increase in viscosity and form a gel at said selected temperature; and
   (d) forming a gel at said selected temperature from said suspension, thereby stabilizing said suspension.

2. The process according to claim 1, wherein said particles are constituted by droplets of a liquid which are not miscible with water and have a dimension between 0.05 microns and 10 microns.

3. The process according to claim 1, wherein said particles are solid particles with a dimension comprised between 0.02 microns and 50 microns.

4. The process according to claim 1, wherein said suspension is a dispersion organized in the form of bilayers.

5. The process according to claim 4, wherein said bilayers are selected from the group consisting of lamellar phases, vesicles and liposomes.

6. A process for stabilizing an aqueous suspension of liposomes having a surfactant present in an amount of about 0.1 to 10% by weight, comprising the step of adding to said suspension an effective amount of a water-soluble associative polymer having a mass average molar mass of about $10^4$ to about $10^7$ and comprising a hydrophilic polymer having intermittent side chains comprising hydrophobic groups containing at least 8 carbon atoms, said amount being effective to cause said suspension to increase in viscosity and form a gel, and forming a gel from said suspension, thereby stabilizing said liposomes in said aqueous suspension.

7. The process according to claim 1, wherein said hydrophilic polymer results from the polymerization of a hydrophilic monomer or is constituted by a water-soluble polymer of natural origin or a natural polymer rendered water-soluble by chemical modification.

8. The process according to claim 1, wherein said hydrophilic polymer comprises an acrylic polymer, a polyether or a polyosidic polymer.

9. The process according to claim 1, wherein the hydrophobic groups are bonded to said hydrophilic polymer by ether, ester or amide groups.

10. The process according to claim 1, wherein said hydrophilic polymer comprises hydrophilic monomers and the proportion of said hydrophobic groups to said hydrophilic monomers is between 0.1% and 10%.

11. The process according to claim 10, wherein said proportion is comprised between 0.5 and 5%.

12. The process according to claim 10, wherein said proportion is comprised between 0.1% and 3%.

13. The process according to claim 1, wherein the hydrophobic groups are hydrocarbon chains, comprising 8 to 28 carbon atoms.

14. The process according to claim 1, wherein said polymer has a mass average molar mass of the order of 150000.

15. The process according to claim 1, wherein said surfactant is selected from the group of surfactants which form liposomes, vesicles or lamellar phases.

16. The process according to claim 1, wherein the composition further comprises a compound in an effective amount for controlling bilayer formation.

17. The process according to claim 16, wherein said compound for controlling bilayer formation is selected from the group consisting of a second surfactant, a fatty alcohol, a sterol, a fatty alcohol phosphate, a sterol phosphate, a fatty alcohol sulphate, a sterol sulphate, a fatty acid, a fatty amine, a saponin, a triterpene derivative, a ceramide, a sphingosine, and mixtures thereof.

18. The process according to claim 1, wherein said surfactant is a polyethylene glycol monoalkylether of general formula:

$$C_iH_{2i+1}(OCH_2CH_2)_jOH$$

where i is between 8 and 18 and j is between 1 and 10.

19. The process according to claim 1, wherein said surfactant is a polyglycerol monoalkylether of formula:

$$R^0O-[C_3H_5(OH)O-]_n-H$$

in which:
  i) $C_3H_5(OH)O$ is represented by one of the following structures, taken as a mixture or separately:

ii) n is an average statistical value between 1 and 6;
  iii) $R^0$ represents:
    a) a Linear or branched, saturated or unsaturated aliphatic chain containing 12 to 30 carbon atoms; or a hydrocarbon radical of a lanolin alcohol; or an α-diol residue;
    b) an $R^1CO$ moiety, where $R^1$ is a linear or branched aliphatic $C_{11}-C_{17}$ radical;
    c) an $R^2-[OC_2H_3(R^3)-]$ moiety, where: $R^2$ has the meaning given in a) or b) for $R^0$;
      $OC_2H_3(R^3)-$ is represented by one of the following structures, taken as a mixture or separately:

$$—OCH—CH_2— \text{ and } —O—CH_2—CH—$$
$$\quad\;\;|\qquad\qquad\qquad\qquad\qquad\quad\;\;|$$
$$\quad R^3\qquad\qquad\qquad\qquad\qquad\quad R^3$$

where $R^3$ has the meaning given in a) for $R^0$; or it may be a linear or branched polyglycerol ether comprising two fatty chains.

20. The process according to claim 1 wherein said surfactant is selected from the group consisting of soaps, lecithins and dialkyldimethylammonium, the alkyl group being a fatty chain having at least 8 carbon atoms.

21. The process according to claim 6 wherein said hydrophilic polymer results from the polymerization of a hydrophilic monomer or is constituted by a water-soluble polymer of natural origin or a natural polymer rendered water-soluble by chemical modification.

22. The process according to claim 6 wherein said hydrophilic polymer comprises an acrylic polymer, a polyether or a polyosidic polymer.

23. The process according to claim 6 wherein the hydrophobic groups are bonded to said hydrophilic polymer by ether, ester or amide groups.

24. The process according to claim 6 wherein said hydrophilic polymer comprises hydrophilic monomers and the proportion of said hydrophobic groups to said hydrophilic monomers is between 0.1% and 10%.

25. The process according to claim 24 wherein said proportion is comprised between 0.5 and 5%.

26. The process according to claim 24 wherein said proportion is comprised between 0.1% and 3%.

27. The process according to claim 6 wherein the hydrophobic groups are hydrocarbon chains, comprising 8 to 28 carbon atoms.

28. The process according to claim 6 wherein said polymer has a mass average molar mass of the order of 150000.

29. The process according to claim 6 wherein the composition further comprises a compound in an effective amount for controlling bilayer formation.

30. The process according to claim 29 wherein said compound for controlling bilayer formation is selected from the group consisting of a second surfactant, a fatty alcohol, a sterol, a fatty alcohol phosphate, a sterol phosphate, a fatty alcohol sulphate, a sterol sulphate, a fatty acid, a fatty amine, a saponin, a triterpene, a ceramide, a sphingosine, and mixtures thereof.

31. The process according to claim 6 wherein said surfactant is a polyethylene glycol monoalkylether of general formula:

$$C_iH_{2i+1}(OCH_2CH_2)_jOH$$

where i is between 8 and 18 and j is between 1 and 10.

32. The process according to claim 6 wherein said surfactant is a polyglycerol monoalkylether of formula:

$$R^0O—[C_3H_5(OH)O—]_n—H$$

in which:
  i) $C_3H_5(OH)O$ is represented by one of the following structures, taken as a mixture or separately:

$$—CH_2CHOHCH_2O—; \quad —CH_2—CHO—;$$
$$\qquad\qquad\qquad\qquad\qquad\qquad\qquad\;\;|$$
$$\qquad\qquad\qquad\qquad\qquad\qquad\quad CH_2OH$$

$$—CH—CH_2O—;$$
$$\;\;|$$
$$CH_2OH$$

ii) n is an average statistical value between 1 and 6;
  iii) $R^0$ represents:
    a) a linear or branched, saturated or unsaturated aliphatic chain containing 12 to 30 carbon atoms; or a hydrocarbon radical of a lanolin alcohol; or an α-diol residue;
    b) an $R^1CO$ moiety, where $R^1$ is a linear or branched aliphatic $C_{11}$–C17 radical;
    c) an $R^2$—[$OC_2H_3(R^3)$—] moiety, where:
    $R^2$ has the meaning given in a) or b) for $R^0$;
    $OC_2H_3(R^3)$— is represented by one of the following structures, taken as a mixture or separately:

$$—OCH—CH_2— \text{ and } —O—CH_2—CH—$$
$$\quad\;\;|\qquad\qquad\qquad\qquad\qquad\quad\;\;|$$
$$\quad R^3\qquad\qquad\qquad\qquad\qquad\quad R^3$$

where $R^3$ has the meaning given in a) for $R^0$;
or it may be a linear or branched polyglycerol ether comprising two fatty chains.

33. The process of claim 6 wherein said surfactant is selected from the group consisting of soaps, lecithins and dialkyldimethylammonium, the alkyl group being a fatty chain having at least 8 carbon atoms.

34. An aqueous gel composition comprising droplets of liquid stabilized by at least one stabilizing agent increasing the viscosity of said composition, wherein said stabilizing agent comprises a combination of:
  (a) at least one non-ionic surfactant in the form of bilayers and, at a concentration comprised between 0.1 and 10% by weight in said composition, said liquid being not miscible in water and said droplets having a dimension in the range of 0.05 microns to 50 microns; and
  (b) a water-soluble associative polymer having a mass average molar mass of about $10^4$ to about $10^7$ and comprising a hydrophilic polymer having intermittent side chains comprising hydrophobic groups containing at least 8 carbon atoms, said surfactants and said associative polymer being present in an amount effective to cause formation of a gel.

35. The composition of claim 34 wherein said droplets are in the form of an oil-in-water emulsion.

36. An aqueous gel composition comprising droplets of liquid stabilized by at least one stabilizing agent increasing the viscosity of said composition, wherein said stabilizing agent comprises a combination of:
  (a) at least one ionic surfactant selected from the group consisting of soaps, lecithins and dialkyldimethammonium, the alkyl group being in fatty chain having at least 8 carbon atoms, said ionic surfactant being in the form of bilayers and at a concentration comprised between 0.1 and 10% by weight in said composition, said liquid being not miscible in water and said droplets having a dimension in the range of 0.50 microns to 50 microns; and
  (b) a water-soluble associative polymer having a mass average molar mass of about $10^4$ to about $10^7$ and comprising a hydrophilic polymer having intermittent side chains comprising hydrophobic groups containing at least 8 carbon atoms, said surfactants and said associative polymer being present in an amount effective to cause formation of a gel.

37. The composition of claim 36 wherein said droplets are in the form of an oil-in-water emulsion.

* * * * *